(12) United States Patent
Pursley

(10) Patent No.: US 7,815,975 B2
(45) Date of Patent: Oct. 19, 2010

(54) CATHETER HAVING POLYMER STIFFENER RINGS AND METHOD OF MAKING THE SAME

(75) Inventor: Matt D. Pursley, Alpharetta, GA (US)

(73) Assignee: Volcano Corporation, Rancho Cordova, CA (US)

(*) Notice: Subject to any disclaimer, the term of this patent is extended or adjusted under 35 U.S.C. 154(b) by 360 days.

(21) Appl. No.: 10/877,524

(22) Filed: Jun. 25, 2004

(65) Prior Publication Data

US 2005/0004556 A1 Jan. 6, 2005

Related U.S. Application Data

(60) Provisional application No. 60/483,474, filed on Jun. 25, 2003.

(51) Int. Cl.
  *B05D 1/02* (2006.01)
(52) U.S. Cl. .................... 427/421.1; 427/2.1; 427/2.25; 427/422
(58) Field of Classification Search ......... 604/524–527; 138/174; 427/2.1, 2.24, 2.25, 2.28, 421.1, 427/427.4, 427.7, 422, 424, 425
See application file for complete search history.

(56) References Cited

U.S. PATENT DOCUMENTS

| | | | |
|---|---|---|---|
| 5,045,072 A | | 9/1991 | Castillo et al. |
| 5,222,949 A | * | 6/1993 | Kaldany ...................... 604/524 |
| 5,364,352 A | * | 11/1994 | Cimino et al. ........... 604/95.04 |
| 5,827,242 A | | 10/1998 | Follmer et al. |
| 5,891,114 A | | 4/1999 | Chien et al. |
| 5,947,940 A | | 9/1999 | Beisel |
| 5,951,539 A | * | 9/1999 | Nita et al. .................... 604/526 |
| 5,954,651 A | | 9/1999 | Berg et al. |
| 6,030,371 A | * | 2/2000 | Pursley ....................... 604/527 |
| 6,097,976 A | * | 8/2000 | Yang et al. .................. 600/373 |
| 6,110,164 A | * | 8/2000 | Vidlund ...................... 604/524 |
| 6,447,488 B2 | * | 9/2002 | Estabrook et al. ........... 604/264 |
| 6,702,972 B1 | | 3/2004 | Markle |

* cited by examiner

*Primary Examiner*—Nicholas D Lucchesi
*Assistant Examiner*—Theodore J Stigell
(74) *Attorney, Agent, or Firm*—Jeffrey L. Thompson; Thompson & Thompson, P.A.

(57) ABSTRACT

A catheter and method of making a catheter are disclosed in which the catheter is highly flexible and yet resistant to crushing and kinking. The catheter is made by applying rings of hard polymer material along the tubular shaft as the catheter is manufactured. The catheter thus has a plurality of hard polymer rings formed at spaced locations along its length, and soft segments between the hard polymer rings that allow the catheter to remain very flexible. The hard polymer rings improve the radial strength of the catheter and make the catheter resistant to crushing and kinking.

11 Claims, 2 Drawing Sheets

CATHETER HAVING POLYMER STIFFENER RINGS AND METHOD OF MAKING THE SAME

RELATED APPLICATIONS

This application claims the benefit of the Applicant's provisional patent Application No. 60/483,474 filed on Jun. 25, 2003.

BACKGROUND OF THE INVENTION

1. Field of the Invention

The present invention relates generally to catheters and, in particular, to catheters that are highly flexible yet resistant to crushing and kinking.

2. Description of the Related Art

Catheters have been developed and are commonly used for a wide variety of medical applications, including interventional therapy, diagnosis, drainage and the like. Catheters can be deployed to numerous target locations within a patient's body by guiding the catheter to the target location. For vascular procedures, catheters may be positioned with the aid of a separate guide wire. Catheters may also be positioned without using a guidewire by forming at least the distal portion of the catheter from a material that is sufficiently soft and flexible to follow blood flow.

Small diameter catheters are commonly used for diagnostic and interventional neurological procedures, such as the diagnosis and treatment of tumors, aneurysms, arteriovenous malformations, and the like. For example, catheters can be used to traverse small blood vessels in the brain vasculature, which are highly tortuous and require that at least a distal portion of the catheters be very flexible to accommodate such tortuosity.

Existing catheters, particularly those used to traverse a tortuous path through the body, suffer from a number of disadvantages. For example, the soft wall of the catheter needed to bend or curve the catheter often becomes crushed or kinked during use, and a small size and tight curvature of the catheter is difficult to achieve. Some manufacturers have used braided or helically wound wires or ribbons within the wall of the catheter to increase the tensile strength and crush resistance of the catheter. Examples of such catheters are disclosed in U.S. Pat. No. 5,954,651 issued to Berg et al., U.S. Pat. No. 5,947,940 issued to Beisel, and U.S. Pat. No. 6,702,972 issued to Markle. Other manufacturers have used slotted metal tubes within their shafts to provide a flexible catheter with good radial strength.

The existing catheters described above often have helical, braided, or other metallic elements embedded into the polymeric wall of the tubular body of the catheter. Such metallic elements create problems because they tend to separate or delaminate from the surrounding polymeric material, particularly in catheters having very thin walls. In an effort to overcome these problems, a catheter having a helical reinforcement element made of a hard polymeric material embedded in the tubular body of the catheter was developed by Follmer et al. and disclosed in U.S. Pat. No. 5,827,242. However, the helical reinforcement layer disclosed by Follmer et al. has not been totally effective in eliminating problems with kinking and crushing of the catheters, particularly in very small diameter catheters.

Thus, there is a need in the industry for an improved catheter that is highly flexible and yet resistant to crushing and kinking during use.

SUMMARY OF THE INVENTION

It is an object of the present invention to provide an improved catheter that is highly flexible and resistant to crushing and kinking during use, which overcomes the problems in the above-mentioned prior art.

It is a further object of the present invention to provide a catheter having hard polymer rings spaced along the length of the catheter to improve the radial strength of the catheter and to prevent crushing and kinking as the catheter is deflected.

It is a further object of the present invention to provide a catheter suitable for traversing a tortuous path through the body without crushing or kinking.

It is a further object of the present invention to provide methods of making an improved catheter having hard polymer rings spaced along its length for improving crush and kink resistance of the catheter while maintaining adequate flexibility.

To achieve the foregoing and other objects and in accordance with the purpose of the present invention, as embodied and broadly described herein, the present invention provides a catheter and method of making a catheter in which the catheter is highly flexible and yet resistant to crushing and kinking. The catheter is made by applying rings of hard polymer material along the tubular shaft as the catheter is manufactured. The catheter thus has a plurality of hard polymer rings formed at spaced locations along its length, and soft segments between the hard polymer rings that allow the catheter to remain very flexible. The hard polymer rings improve the radial strength of the catheter and make the catheter resistant to crushing and kinking.

In accordance with a broad aspect of the present invention, a catheter is provided comprising: a tubular member formed of a soft, flexible polymer material; and a plurality of hard polymer rings disposed at spaced locations along a length of the tubular member. Methods of making such a catheter are also provided.

According to another broad aspect of the present invention, a catheter is provided that is highly flexible yet resistant to crushing and kinking, comprising: a tubular member formed of a soft, flexible polymer material having a hardness within a range of about 80 Shore A to 35 Shore D; and a plurality of hard polymer rings which are concentric with the tubular member and disposed at spaced locations completely separated from each other along a length of the tubular member, the hard polymer rings being formed of a polymer material having a hardness greater than about 70 Shore D and being spaced apart from each other a distance within a range of about 0.1 to 1.0 times the diameter of the tubular member.

Additional objects, advantages, and novel features of the invention will be set forth in the following description, and will become apparent to those skilled in the art upon reading this description or practicing the invention. The objects and advantages of the invention may be realized and attained by the appended claims.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

Figure 1:
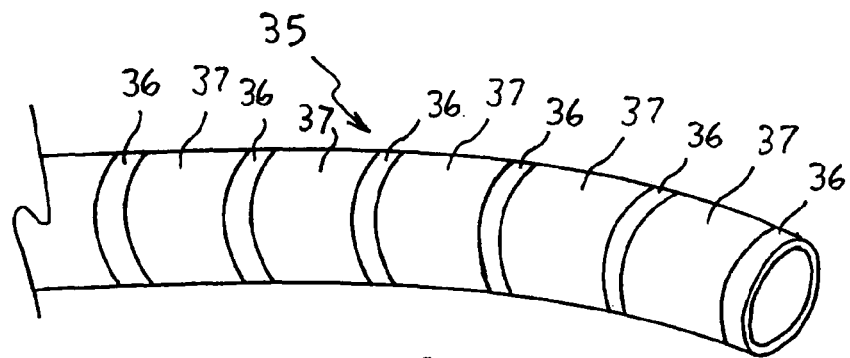
FIG. 1 is a perspective view of a catheter according to the present invention in which a plurality of hard polymer rings are spaced along the length of the catheter to increase radial strength and resist crushing and kinking.
Figure 2:
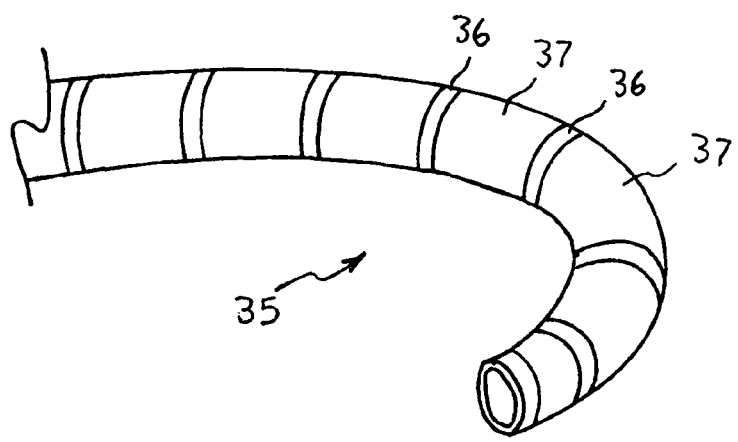
FIG. 2 is a perspective view of the catheter shown in FIG. 1 with a curvature introduced at the distal end.

A catheter 35 according to the present invention will now be described with reference to FIGS. 1 to 4 of the accompanying drawings.

The catheter 35 has an inner tubular member 35i formed of a soft polymer material, such as nylon, urethane, PE or TFE, which is flexible and can be easily bent as it traverses a tortuous path within the body. The soft polymer material will typically have a hardness within a range of 80 Shore A to 35 Shore D.

A plurality of hard polymer rings 36 are formed along the inner tubular member 35i of the catheter 35. The hard polymer rings 36 are concentric about the axis of the inner tubular member 35i and function to increase the radial strength of the catheter 35 and resist crushing or kinking. The hard polymer rings 36 are spaced so that the soft segments 37 of the catheter 35 between the rings 36 cause the catheter 35 to remain very flexible. The hard polymer rings 36 can be formed, for example, of epoxies, cyanoacrylicates, acrylics and other suitable polymeric materials having a hardness greater than about 70 Shore D. For example, UV-cured epoxies that get hard when exposed to UV light are particularly suitable for use as the hard polymer rings 36.

The hard polymer rings 36 will normally be spaced apart from each other a distance equal to about 0.1 to 1.0 times the diameter of the catheter tube. The hard polymer rings 36 will have a width of about 0.010 to 0.050 inch and a thickness of less than about 0.001 inch. The dimensions and spacing of the hard polymer rings 36 will be dictated mainly by the required bend radius and diameter of the catheter 35. For example, a wider spacing and/or narrower width of the hard polymer rings 36 may be used to accommodate a tighter bending radius. Also, the spacing and/or width of the hard polymer rings 36 can be varied over the length of the catheter 35 to accommodate a more rigid structure at the proximal end and a more flexible structure at the distal end. The hard polymer rings 36 will cover approximately 30 to 80% of the length of the catheter. For example, the hard polymer rings 36 will cover about 50% of the length of the catheter when the width of the hard polymer rings 36 is equal to the spacing between the hard polymer rings 36 (i.e., in the case where the width of the hard polymer rings 36 is equal to the width of the flexible portions 37 between the hard polymer rings 36).

Figure 3:
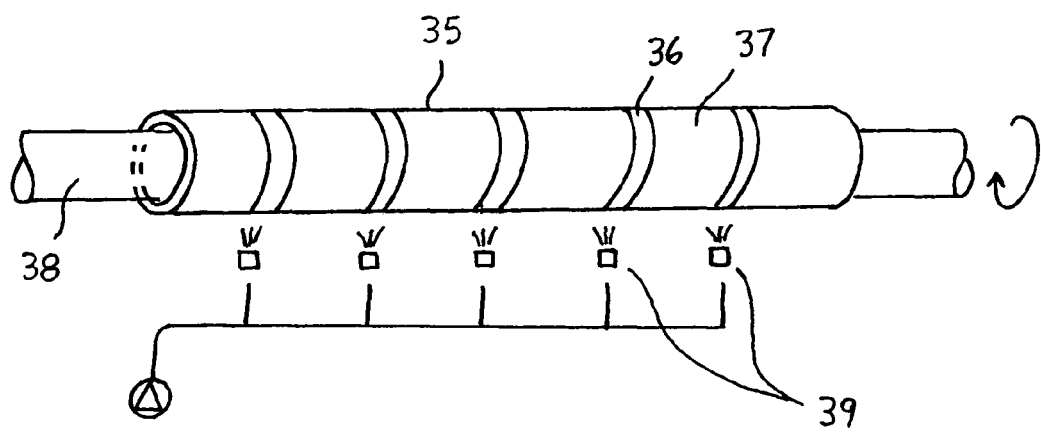
FIG. 3 is a perspective view of a catheter manufacturing process in which rings of hard polymer are applied along the shaft of the catheter as the catheter is being manufactured.

The catheter 35 according to the present invention can be made, for example, by adapting and using the nonextrusion manufacturing method and apparatus described in the Applicant's U.S. Pat. No. 6,030,371 based on the teachings herein. As shown in FIG. 3, the hard polymer rings 36 can be formed on the inner tubular member 35i of the catheter 35 using a rotating mandrel 38 with a plurality of spray heads 39, brushes, rollers, or the like, which apply the hard polymer to the outer surface of the inner tubular member 35i. A suitable top coat 40 is then applied over the outer surface of the catheter 35 to cover both the hard polymer rings 36 and the soft segments 37 of the inner tubular member 35i between the rings 36 to create a seamless end product.

Other methods can also be used to fabricate the catheter 35 according to the present invention. For example, the hard polymer rings 36 could be laminated between layers during an otherwise conventional extrusion manufacturing process of making catheters.

Figure 4:
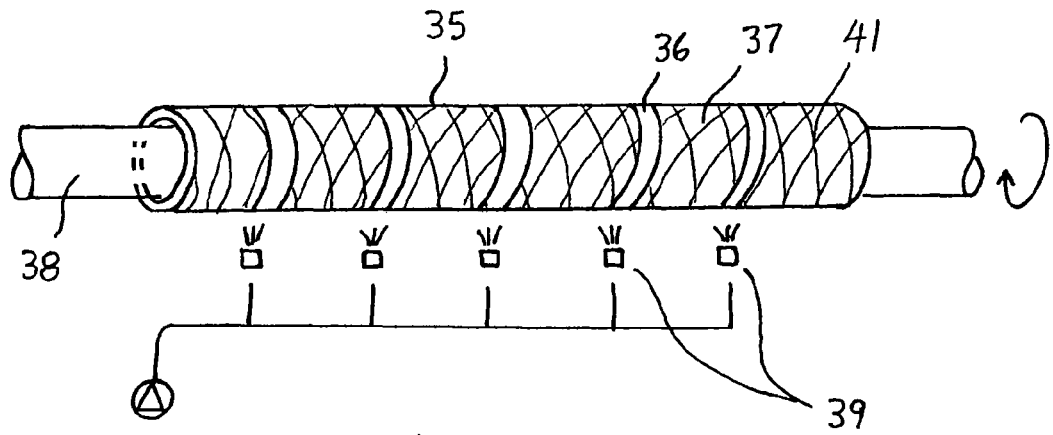
FIG. 4 is a perspective view of a catheter manufacturing process in which a fibrous reinforcement layer is applied to the catheter before the rings of hard polymer are applied.
Figure 5:
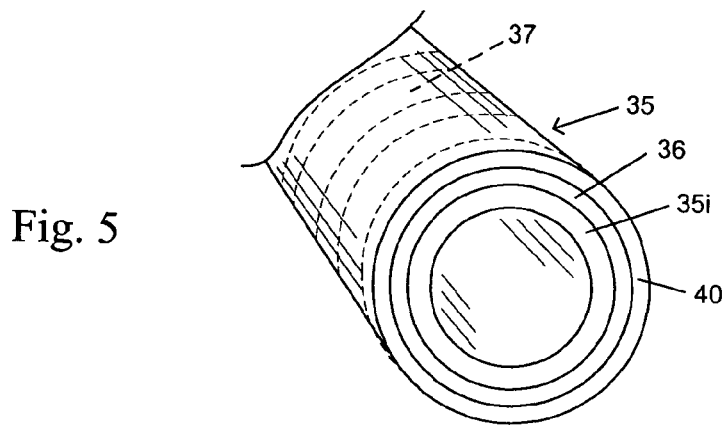
FIG. 5 shows the various layers of the catheter according to the present invention as viewed in cross section at the location of the hard polymer rings.
Figure 6:
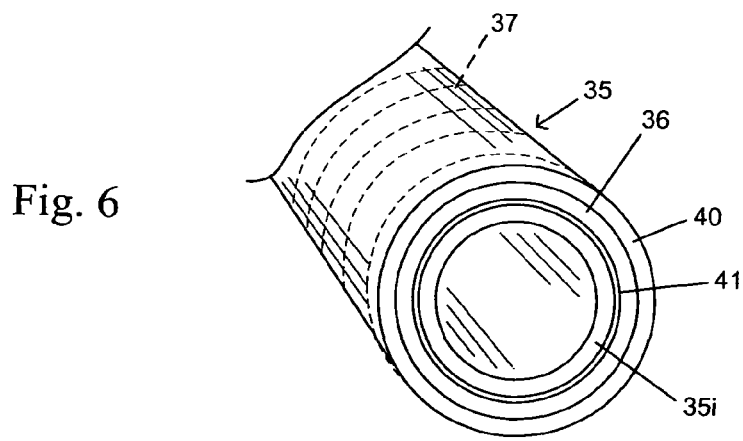
FIG. 6 shows the various layers of a catheter in which the hard polymer rings are applied over a layer of fibrous reinforcement material.

In another embodiment, as shown in FIG. 4, the polymer rings 36 are applied over a conventional reinforcement layer 41 of braided or helically wound filament. By applying the hard polymer in a liquid state, e.g., by spraying using spray heads 39, the hard polymer material will cover the filament winding 41 and also seep around and under the individual strands of the filament winding 41 before curing, thereby creating a sturdy anchor for the hard polymer rings 36. A suitable top coat 40 is then applied over the outer surface of the catheter 35 to cover both the hard polymer rings 36 and the filament winding 41.

In another embodiment, one or more of the hard polymer rings 36 is formed by adding an opacifier to the hard polymer material before the material is applied to the catheter 35. The opacifier can be, for example, barium sulfate, tungsten, or other suitable radiopaque agent. The hard polymer ring(s) with an opacifier added will serve as a marker that is readily visible by x-ray during a medical procedure.

The hard polymer rings 36 are effective to prevent crushing and resist kinking of the catheter 35 during use. The hard polymer rings 36 do not restrict the bending radius and flexibility of the catheter 35 because the rings 36 are completely separated by the soft flexible material 37. As a result, the hard polymer rings 36 offer a substantial improvement over conventional catheters that rely only on helical or braided filament windings for kink and crush resistance.

Although this application describes catheters used to perform medical procedures, it will be appreciated that the invention may have application to other tubular structures that need crush and kink resistance while maintaining a high flexibility. The term "catheter" as used herein is intended to cover all such tubular structures.

While the invention has been specifically described in connection with specific embodiments thereof, it is to be understood that this is by way of illustration and not of limitation, and the scope of the appended claims should be construed as broadly as the prior art will permit.

What is claimed is:

1. A method of making a catheter, comprising the steps of:
providing an inner tubular member of a soft, flexible polymer material; and
spraying a hard polymer material on an outer surface of said tubular member to form a plurality of hard polymer rings on said outer surface of said inner tubular member at spaced locations along a length of the tubular member, said hard polymer material having a hardness greater than said soft, flexible polymer material to provide resistance to crushing and kinking, wherein said hard polymer rings are formed concentric with the tubular member and are completely separated from each other.

2. The method of making a catheter according to claim 1, further comprising the step of applying a top coat over the hard polymer rings and the tubular member to create a seamless end product.

3. The method of making a catheter according to claim 1, wherein said step of forming a plurality of hard polymer rings comprises applying a hard polymer in liquid form to the outer surface of the tubular member.

4. The method of making a catheter according to claim 1, wherein said hard polymer rings are formed of a polymer material having a hardness greater than about 70 Shore D, and said soft, flexible polymer material has a hardness of less than about 35 Shore D.

5. The method of making a catheter according to claim 1, wherein said hard polymer rings are formed to cover approximately 30 to 80% of the length of the catheter.

6. The method of making a catheter according to claim 1, wherein said hard polymer rings are formed on the tubular member with a spacing between adjacent rings of about 0.1 to 1.0 times the diameter of the tubular member.

7. The method of making a catheter according to claim 1, wherein said hard polymer rings are formed on the tubular member with a spacing between adjacent rings that varies over a length of the catheter.

8. The method of making a catheter according to claim 1, wherein said hard polymer rings are formed on the tubular member with a width of about 0.010 to 0.050 inch.

9. The method of making a catheter according to claim 1, wherein said hard polymer rings are formed of a material selected from the group consisting of epoxies, cyanoacrylicates and acrylics.

10. The method of making a catheter according to claim 1, wherein at least one of said hard polymer rings is formed by mixing an opacifier material with a polymer material to make the at least one hard polymer ring readily visible by x-ray.

11. The method of making a catheter according to claim 1, further comprising the step of applying a fibrous reinforcement layer over the tubular member and then forming said hard polymer rings over said fibrous reinforcement layer by spraying the hard polymer material so that said hard polymer material seeps around and under individual strands of the fibrous reinforcement layer to create a sturdy anchor for the hard polymer rings.

\* \* \* \* \*